(12) United States Patent
Menashi et al.

(10) Patent No.: US 6,265,884 B1
(45) Date of Patent: Jul. 24, 2001

(54) ELECTRICAL CONDUCTIVITY GEM TESTER

(75) Inventors: Solomon Menashi, Newton, MA (US); David Barrett, Grand Island, NY (US); Wayne Duderwick, Williamsville, NY (US); Randolph M. Bogdan, West Seneca, NY (US)

(73) Assignee: Ceres Corporation, Niagara Falls, NY (US)

( * ) Notice: Subject to any disclaimer, the term of this patent is extended or adjusted under 35 U.S.C. 154(b) by 0 days.

(21) Appl. No.: 09/310,400

(22) Filed: May 12, 1999

Related U.S. Application Data

(60) Provisional application No. 60/085,300, filed on May 13, 1998.

(51) Int. Cl.[7] ............................. G01N 27/02; G01N 27/92
(52) U.S. Cl. ......................... 324/717; 324/693; 324/722; 324/71.1
(58) Field of Search .................................... 324/691, 693, 324/705, 713, 715, 717, 722, 71.1

(56) References Cited

U.S. PATENT DOCUMENTS

| 3,944,922 | 3/1976 | Chambers et al. ................. 324/158 P |
| 4,255,962 | 3/1981 | Ashman ................................. 73/15 A |
| 4,324,129 | 4/1982 | Goldsmid ............................. 73/15 A |

(List continued on next page.)

OTHER PUBLICATIONS

Wedlock, B.D. and Roberge, J.K., "Resistors" in *Electronic Components and Measurements*, (N.J., Prentice–Hall, Inc.), pp.82–88 (1969). (Month unavailable).

*Primary Examiner*—Glenn W. Brown
(74) *Attorney, Agent, or Firm*—Hamilton, Brook, Smith & Reynolds, P.C.

(57) ABSTRACT

It has been learned that moissanite and other synthetic stones, including synthetic moissanite and synthetic diamond, are distinguishable from natural diamonds based on differing electrical conductivities. The present invention, therefore, provides an apparatus and method for determining a gem type based on its electrical conductivity. In particular, an electronic circuit including the gem under test as part of a circuit path is used to measure its electrical conductivity and, therefore, gem type. The onerous task of determining whether a gem is moissanite or synthetic diamond involves providing a high voltage across a gem surface greater than a breakdown voltage, typically greater than 300 volts, and measuring a minuscule current that flows through the gem. A first and second contact couple the high voltage to the gem under test, where a low impedance detection circuit is used to flag when the contacts are erroneously contacting each other during a measurement. Sampling techniques are employed to avoid false readings based on AC coupled noise and an optional conductive block with holes or cavities is used to retain loose gems during the testing process.

50 Claims, 12 Drawing Sheets

U.S. PATENT DOCUMENTS

| | | | |
|---|---|---|---|
| 4,344,315 | 8/1982 | Moxon et al. | 374/44 |
| 4,364,677 | 12/1982 | Ashman | 374/44 |
| 4,488,821 | 12/1984 | Wenckus | 374/44 |
| 4,616,939 | 10/1986 | Gitlis | 374/44 |
| 4,646,571 | 3/1987 | Kising et al. | 73/573 |
| 4,841,764 | 6/1989 | Fischer | 73/81 |
| 4,898,470 | 2/1990 | Cleaveland | 356/359 |
| 4,906,083 | 3/1990 | Sattler | 350/524 |
| 5,052,819 | 10/1991 | Baratta | 374/43 |
| 5,118,181 | 6/1992 | Yifrach et al. | 356/30 |
| 5,317,275 | 5/1994 | Mount et al. | 324/692 |
| 5,358,596 | 10/1994 | Cappelli et al. | 117/99 |
| 5,379,102 | 1/1995 | Takeuchi | 356/30 |
| 5,450,745 | 9/1995 | Flaherty | 73/82 |
| 5,533,411 | 7/1996 | Koiwa | 73/598 |
| 5,536,943 | 7/1996 | Smith et al. | 250/372 |
| 5,559,436 | 9/1996 | Matthews et al. | 324/236 |
| 5,603,414 | 2/1997 | Rooney et al. | 209/588 |
| 5,620,253 | 4/1997 | Graebner et al. | 374/43 |
| 5,664,884 | 9/1997 | Graebner et al. | 374/43 |
| 5,703,288 | 12/1997 | Horiguchi et al. | 73/204.26 |
| 5,748,317 | 5/1998 | Maris et al. | 356/357 |
| 5,756,893 | 5/1998 | Kondo et al. | 73/204.22 |
| 5,801,819 | 9/1998 | Spear et al. | 356/30 |
| 5,807,523 | 9/1998 | Watts et al. | 422/64 |
| 5,811,817 | 9/1998 | Ravich | 250/372 |
| 5,811,824 | 9/1998 | Smith et al. | 250/559.4 |
| 5,835,200 | 11/1998 | Smith et al. | 356/30 |
| 5,835,205 | 11/1998 | Hunter et al. | 356/30 |
| 5,844,684 | 12/1998 | Maris et al. | 356/432 |
| 5,880,504 | 3/1999 | Smith et al. | 250/372 |
| 5,955,735 * | 9/1999 | Coleman | 324/133 X |

* cited by examiner

ELECTRICAL CONDUCTIVITY GEM TESTER

RELATED APPLICATION

This application claims the benefit of U.S. Provisional Application Ser. No. 60/085,300 filed on May 13, 1998 entitled "Electrical Conductivity Gem Tester," the entire teachings of which are herein incorporated by reference.

BACKGROUND OF THE INVENTION

Diamonds have an allure unlike any other gemstone. Through the ages, they have been sought after for their characteristically brilliant qualities and have been the subject of great treasures. There is such high demand for the stones, even today, that considerable research is under way to produce synthetic gems.

Gemstones such as cubic zirconium and silicon carbide, also known as moissanite, have become increasingly popular because they are almost indistinguishable from real diamonds with the naked eye. As a result, the market is flooded with these synthetic look-alike gemstones. Unfortunately, some of these gemstones, significantly lower in value, are sold as natural diamonds to the dismay of many unknowing purchasers. To combat these fraudulent or mistaken sales, several techniques have been suggested to determine the authenticity of a diamond.

One technique involves a relatively complex x-ray test that takes several hours to perform. Unfortunately, the associated testing apparatus is costly and most jewelers are not equipped with the instrumentation required to perform the test. Another technique involves testing the hardness of the gemstone by scratching or otherwise marring the surface of the gem. Needless to say, this method of defacing a gem is highly undesirable because it negatively impacts the value of the gem and alternative nondestructive methods of testing are available today.

Alternative non-destructive test methods include testing the optical transmissivity and thermal characteristics of a gem to determine whether it is a real diamond. In particular, one optical method involves transmitting light waves through the gem under test and, thereafter, determining which wavelengths of the light source have been absorbed. Generally, diamonds reflect certain wavelengths of light while silicon carbide absorbs certain wavelengths of light. Unfortunately, determining the authenticity of a diamond based on this method is not failsafe because the transmissivity of some diamonds is effected by their cut and mass.

Another non-destructive method of determining the authenticity of a diamond involves testing the thermal conductivity of the gem. The test process includes heating a probe of known mass to a predetermined level and touching the probe to the gem under test. A thermistor in the probe is used to detect the dynamic change in probe temperature as the gem absorbs heat energy from the probe thereby reducing its temperature; i.e. the temperature of the probe gradually decreases depending on the rate at which heat is absorbed by the gem under test. Based on the rate of temperature change of the probe, the thermal conductivity of the diamond is determined and, thus, whether the gem under test is a real diamond. The thermal conductivity test is widely used to distinguish cubic zirconia and diamond, but silicon carbide has a thermal conductivity which is about equal to that of diamond, making the test impractical for those gemstones.

Electrical resistance measurements have been used to distinguish gems. In particular, some thermal testers have included a two electrode device for detecting when a thermal test probe is erroneously in contact with a metal, which has a thermal conductivity very similar to that of natural diamonds. This prevented an operator from falsely identifying a gemstone as diamond when, in fact, the measuring device was measuring the thermal conductivity of the metal instead of the gem. Occasionally, this low impedance detection circuit, when used correctly, could positively indicate that a gem under test was a member of a more conductive class of moissanite. The tester, however, was unsuccessful at identifying the balance of moissanite gems that were less conductive.

Since the value of a diamond is in part dependent upon its weight, it is not uncommon to increase its size and, therefore, apparent value, by depositing simulant diamond material on an uncut or partly cut natural diamond. This combination, namely real and imitation diamond, is particularly difficult to distinguish from a completely natural diamond because in some respects the imitation-natural stone has qualities of a natural diamond while in other respects the imitation-natural stone has the qualities of a synthetic stone.

SUMMARY OF THE INVENTION

Most electrical meters are unable to distinguish gem impedances because the impedances are typically well above 10 meg-ohms. Some classes of synthetic gems can be distinguished if they have a low enough impedance, but this is rare. Based on lower voltage measurement systems, moissanite and natural diamonds are practically indistinguishable because neither gem type conducts electricity at these lower measuring voltages.

The present invention provides an apparatus and method for determining a gem type based on its electrical conductivity. In particular, an electronic circuit including the gem under test as part of a circuit path is used to measure its electrical conductivity and, therefore, gem type.

Moissanite and synthetic diamonds are distinguishable from natural diamonds based on differing electrical conductivities. Natural diamond stones are virtually non-conductive whereas moissanite and synthetic diamonds are slightly conductive when a high voltage greater than a breakdown voltage, inducing a small current to flow, is applied across the surface of the gem under test. The resistivity of moissanite or a synthetic diamond exposed to a voltage above the breakdown voltage is typically between 1 and 2000 mega-ohms, which is very difficult to measure with state of the art measuring devices. The present invention addresses the onerous task of determining whether a gem is moissanite or synthetic by providing a high voltage across a gem surface, typically greater than 300 volts, and measuring a minuscule current that flows through the gem.

A high voltage, including a high impedance source, applied between a first and second electrode contacting the gem under test induces a current to flow through the gem to a return reference voltage such as ground. The amount of current flowing through the device is measured using, for example, a high impedance resistor referenced to ground. A voltage on the resistor, indicative of the current flowing through the gem, is measured and compared to a predetermined threshold voltage. Measurements above the threshold voltage indicate that the gem is conductive and that the gem, therefore, is a synthetic diamond or moissanite. Conversely, measurements below a threshold voltage indicate that practically no current flows through the gem and that the gem, therefore, may be a diamond if other tests such as a visual and thermal conductivity tests are positive.

In the preferred embodiment, the gem is part of a resistor divider circuit, where distinguishing audio and visual queues are used to alert an operator whether a gem positively tests to be moissanite or a synthetic diamond.

The present invention also addresses when the impedance between the electrodes is so low that a material disposed between the electrodes is not moissanite or a synthetic diamond stone. For instance, it is possible that the test electrodes are erroneously connected to each other directly through a gem mount or that the purported gem is made of conductive plastic.

In the preferred embodiment, the current through the electrodes is limited so that a person accidentally in contact with the electrodes neither feels a shock nor is harmed by the voltage at the electrodes. Typically, the maximum safe and undetectable current through a human disposed between the electrodes is 150 micro-amps. This current limiting feature also protects the gem from damage.

The gem under test is optionally tested in a number of ways. A first method involves contacting the two electrodes at two different points on the gem under test. A second method involves connecting one electrode, such as a clip, to a conductive setting of gem and contacting the second electrode to the surface of the gem under test to create a circuit path with the gem disposed between the first and second electrodes. A third method involves providing cavities or holes in a conductive block for cupping or retaining loose gemstones, where a circuit path through the gem is created by contacting a first electrode on the conductive block which, in turn, is in contact with the retained gem and contacting a second electrode on the surface of the gem under test.

High impedance measurements in the present invention are sometimes susceptible to AC coupling noise that deleteriously affects sample voltage measurements used to determine conductivity and gem type. This is due to the fact that the gem tester measuring device measures a very high impedance using high impedance probe inputs. Measurements, therefore, are particularly susceptible to stray noise or AC coupling. In the preferred embodiment of the present invention, repeated sample measurements of a particular gemstone assure that a single measurement based on a glitch in the measured voltage does not cause erroneous readings. The preferred method requires that a predetermined number of consecutive samples be above a threshold before a gem is determined to be moissanite or synthetic diamond.

It has been learned that there are sometimes non-conductive zones in moissanite gemstones. As a result, the gem tester of the present invention may erroneously determine that a moissanite sample, appearing non-conductive because an electrode is contacting a non-conductive zone, is not moissanite. This obstacle may be overcome by marking the gem under test with a conductive material, such as a water-based marker, to bridge any non-conductive zones on a gem that may be made of moissanite.

An electrode in contact with the marked surface, therefore, is more likely to positively identify whether a gem is moissanite or a synthetic gem.

The aforementioned features of the present invention advantageously describe an apparatus and method for non-destructively determining the authenticity of a gemstone based on electrical conductivity.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

A key aspect of the present invention involves testing the electrical conductivity of a gem to determine with a high likelihood whether it is Silicon Carbide (SiC), otherwise known as moissanite, or a synthetic diamond gem.

There are several synthetic look-alike diamond gemstones on the market, all of which have significantly less value than natural diamonds. If the electrical conductivity tester of the present invention does not indicate that a gem under test is a moissanite or synthetic diamond stone, it is likely a natural diamond, cubic zirconia or glass. Further testing of the stone provides a means of distinguishing diamonds from cubic zirconia stones, where the testing process is based on the principle that the thermal conductivity of a diamond is much higher than that of cubic zirconia. In fact, a natural diamond apparently has the highest thermal conductivity of any gemstone in the world.

To reliably determine whether a gem is synthetic, it is necessary that an electrical conductivity tester measure electrical resistance within a range of about 1 to 20,000 mega-ohms when measured at a high voltage. Moissanite gems of this type apparently have a breakdown voltage requiring an approximate minimum voltage of 300–500 volts to consistently obtain a conductivity measurement. At lesser voltages, moissanite may appear as a high electrical impedance approximating that of diamond. Conventional ohm-meters, such as those based on 30 volts, therefore, typically can not distinguish moissanite or a synthetic diamond from an open circuit. The higher voltage mega-ohm testers will enable detection of the higher resistance stones, but may fail to distinguish a synthetic stone from metal. To measure gem resistance as high as up to 20,000 mega-ohms with a simple voltage divider circuit, it has been determined that a voltage of at least 500 volts should be applied to the voltage divider which includes a circuit through the gem under test, where at least 300 volts appears across the gem under test. The voltage causes a current to flow through the gem which is limited by the voltage divider circuit.

To avoid resistance changes in the gem due to loss of minority carriers, the current should be less than 75 microamps, preferably less than 10 microamps. This low current, preferably below 150 microamps, also prevents harm to a user accidentally disposed between two conductive contacts used to couple the high voltage across the gem under test.

Figure 1:
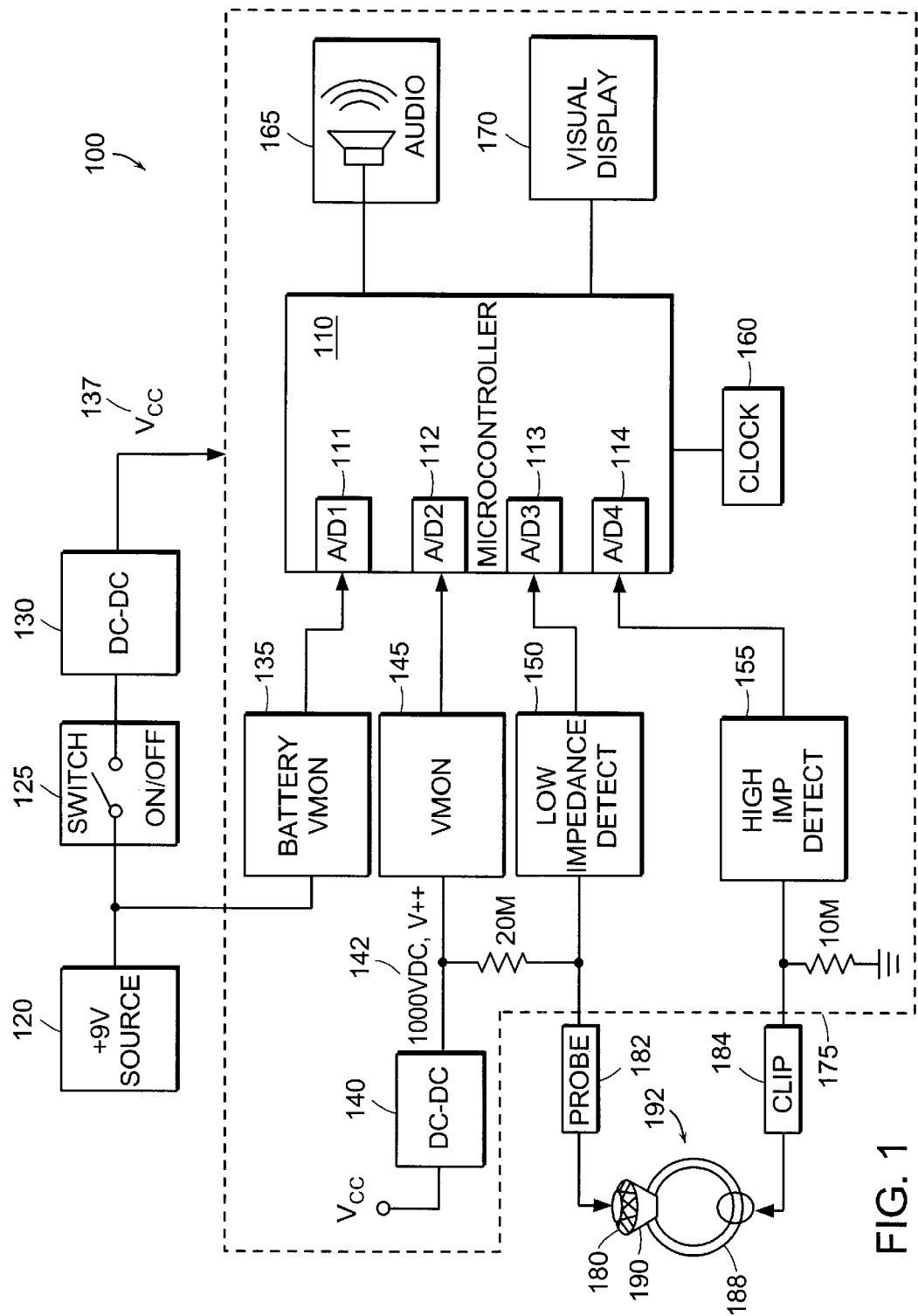
FIG. 1 is a block diagram of the Electrical Conductivity Gem Tester according to the present invention.

FIG. 1 shows the connectivity of functional blocks according to the principles of the present invention. At the core of the gem tester 100 is a microcontroller 110 for processing a plurality of analog input voltages to produce a number of outputs indicative of whether a measurement for a gem under test 190 is in fact within a specific range indicating that it is moissanite or a synthetic diamond stone. In the preferred embodiment, the microcontroller 110 is a Motorola 68HC705P6A. However, any suitable processing device is optionally used in its place.

It is contemplated that the individual components such as the functional elements of the invention are optionally partitioned or integrated into one or many devices to achieve the principles of the present invention. For example, an alternate data processing device and discrete A/D converters are optionally used in place of the preferred micro-controller including a plurality of integrated A/D converters.

Every micro-controller requires a clock to operate. In the present invention, a system clock 160 provides the toggles or clock transitions necessary for executing binary operational instructions and performing A/D conversions within micro-controller 110. In the preferred embodiment, a ceramic resonator provides the precise external frequency source used as the system clock 160.

In the preferred embodiment, the gem tester 100 is portable. A +9V source 120 from a battery or wall adapter converter (i.e., 115 VAC to +9 VDC converter), therefore, is used to power the device for convenience. ON/OFF switch 125, preferably a single pole single throw mechanical switch, provides a means of controlling the connectivity of the battery 120 to the low voltage DC-DC converter 130. The ON/OFF switch 125 is typically mechanical, but it is optionally an electrical component such as a FET.

The low voltage DC-DC converter 130, as its name suggests, converts the voltage from the +9V source 120 to an acceptable voltage for powering analog and digital circuitry. Typically, the Vcc circuitry voltage is near +5 VDC but the attributes of the present invention can be achieved even if the electronic circuitry in the gem tester 110 is designed around a +3V system. For example, low voltage/power analog and digital devices that operate in the +3 volt range are optionally used. In such a case, the low voltage DC-DC converter would be designed to support the lower voltage devices; namely, Vcc would be set at approximately +3 VDC.

In the preferred embodiment, a standard voltage regulator is used to regulate down the +9V source 120 voltage to Vcc or +5 VDC voltage. However, it should be noted that other converters are optionally used to achieve the same result. The output voltage, Vcc 137, of the low voltage DC-DC converter 130 provides power to the electronic circuitry within dotted line 175.

A battery voltage monitor 135 is provided to detect a low voltage condition of the +9V source 120 voltage. As shown, the raw +9V source 120 voltage is fed into monitor circuit 135, where a circuit is designed to condition the signal for processing within the micro-controller 110. If a low voltage condition is detected, a visual display 170, such as an LED, is optionally lit or audio speaker 165 optionally sounded to indicate the faulty low voltage condition to the operator of the gem tester 100. Internally, the microcontroller 110 will discontinue gem testing when the voltage source input to the gem tester is below a certain threshold such as 7.5 VDC.

A low-to-high DC-DC converter 140 provides the high voltage source V++ 142 for determining the electrical conductivity of the gem under test. As shown, an input voltage Vcc 137, i.e., +5 VDC, is converted to a voltage in excess of 300 VDC. In the preferred embodiment, the high voltage source V++ 142 is set between 900 and 1000 VDC. However, any high voltage, AC or DC, greater than 300 volts is optionally used to achieve the same results.

The high voltage source V++ 142 from the low-to-high voltage DC-DC converter 140 is fed into voltage monitor 145. This functional block includes a means for stepping down the voltage to a level that is reasonably handled by A/D2 112 in the microcontroller 110. If the high voltage 142 was fed directly into the A/D converter in the microcontroller 110, it would potentially damage the device since it is well in excess of Vcc.

The high voltage V++ 142 is proportionally lowered such that a voltage on the output of the voltage monitor 145 between 0–2.5 volts linearly reflects the range of 0–1000 VDC on the original high voltage source 142 input.

Based on the linearity of input to output of the voltage monitor 145, the microcontroller 110 determines whether the high voltage source V++, namely 1000 VDC, is within a tolerable range. If not, the microcontroller 110 notes the error and optionally conveys the fault to the operator using a visual display 170 or audio indicator 165.

A purported diamond ring 192 is tested by placing probe 182 in contact with the gem under test 190 at contact point 180. The probe 182 is electrically connected to low impedance detection circuit 150 that provides a means of determining whether the electrical conductivity of the purported diamond ring 192 between the probe 182 and clip 184 is so low as to indicate a faulty test setup. For example, when the probe 182 and clip 184 are both connected to the metallic ring 188, a low impedance, the operator is alerted by a buzzer about the faulty setup condition.

The clip electrode 184 in contact with the metallic portion 188 of the purported diamond ring 192 provides a return path for the high voltage applied by the probe 182. In other words, the probe 182 provides a high voltage, high impedance current source, where current travels through the gem under test 190 and the metallic portion 188 of the purported diamond ring 192 to the clip and eventually back to ground through a high impedance return path in the high impedance detection circuit 155. The voltage output of the high impedance detection circuit is fed into A/D #4 input 114 to determine whether the analog signal indicates that the gem is moissanite or synthetic diamond gem. This process will be described in more detail in connection with other figures below.

FIG. 2A through 2E illustrate the preferred electronics of the present invention. It should be noted that alternate electronic circuitry is optionally designed to achieve the principles of the present invention. For example, an alternate type of DC-DC converter, such as a switching power supply, is optionally used in lieu of the circuitry discussed herein.

Note that the signal names used in the individual schematics, as in FIG. 2A through 2E, indicate where electrical nodes are interconnected between schematic pages. Hence, the schematics in FIG. 2A through 2E define multiple interconnected circuits residing on one or a number of PC boards.

Figure 2A:
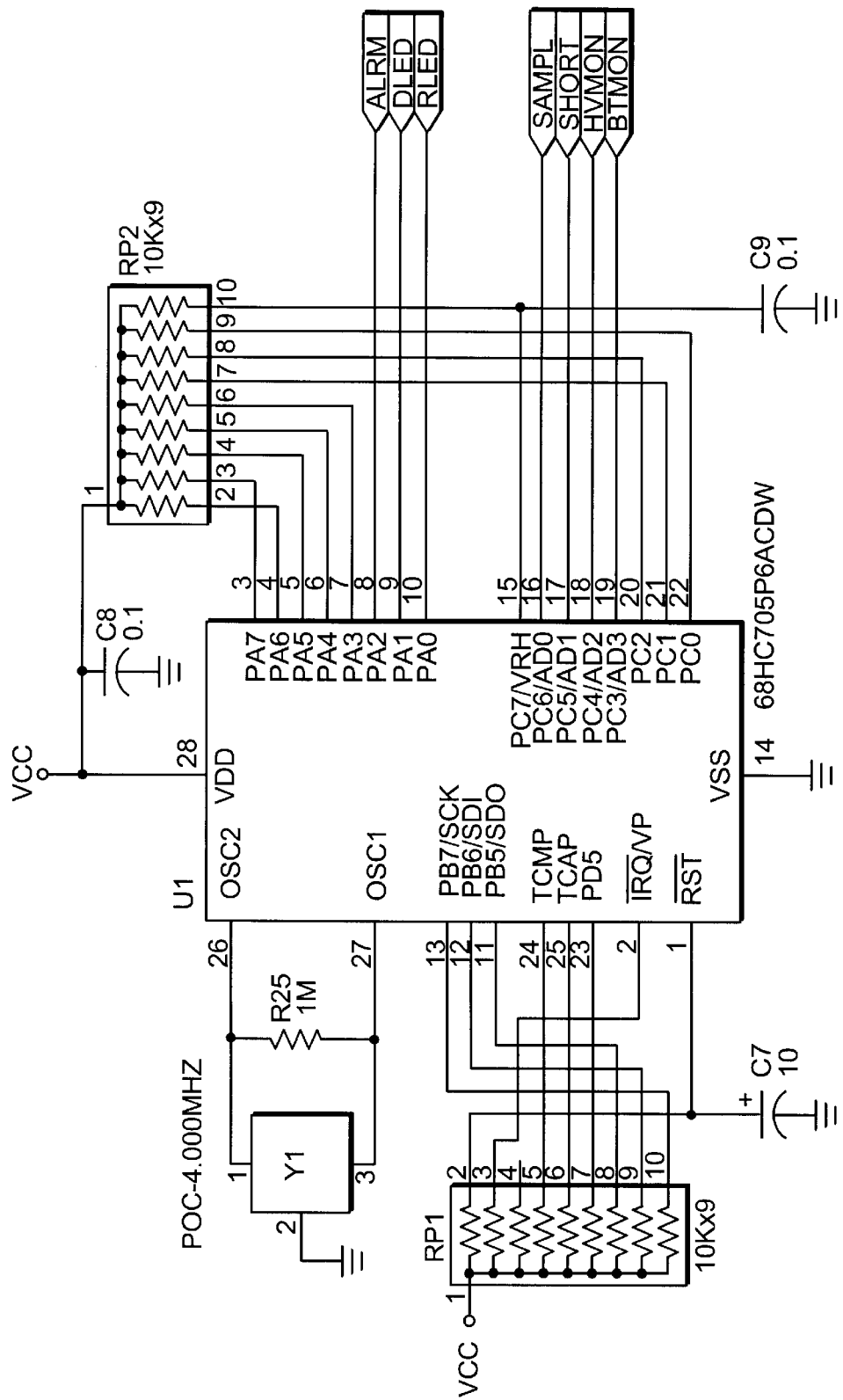
FIG. 2A is an electronic schematic of the micro-controller and related circuitry of the present invention.

At the center of FIG. 2A is microcontroller U1. As mentioned, it includes a specific set of operational instructions or software code to determine whether a gem under test 190 is moissanite or a synthetic diamond stone. In particular, four separate input voltages are converted into binary data, the contents of which are processed to determine whether the gem under test is moissanite or a synthetic diamond stone.

A first input, BTMON, is a voltage signal proportional to the voltage on the +9V source power 120. A second input, HVMON, reflects the health of the high voltage power source. Based on the conversion of both signals, the health of the gem tester unit is analyzed. If either input voltage falls outside a tolerable range, the microcontroller will flag the error and discontinue testing. Effectively, the microcontroller U1 calls into question the accuracy sample measurements if the system fails this preliminary diagnostic self test. Put simply, if these voltages are too low, part of the circuitry is malfunctioning and, therefore, any measurements with the gem tester device will likely be inaccurate.

The SAMPLE and SHORT signal inputs, on U1 pin 16 and 17 respectively, provide the micro-controller U1 with two voltage signals indicative of whether or not a gem under test is a moissanite or a synthetic diamond stone. A/D conversions on these signals, presuming that abovementioned HVMON and BTMON indicate a healthy gem tester status, are processed and the appropriate outputs, ALRM, DLED and RLED are controlled to produce an audio or visual clue for an operator, reflecting whether the gem under test is moissanite or a synthetic diamond stone. Y1 is a 4.0 MHZ crystal oscillator that provides the microcontroller U1 with a timing mechanism for executing operational instructions and A/D conversions within the microcontroller.

Figure 2B:
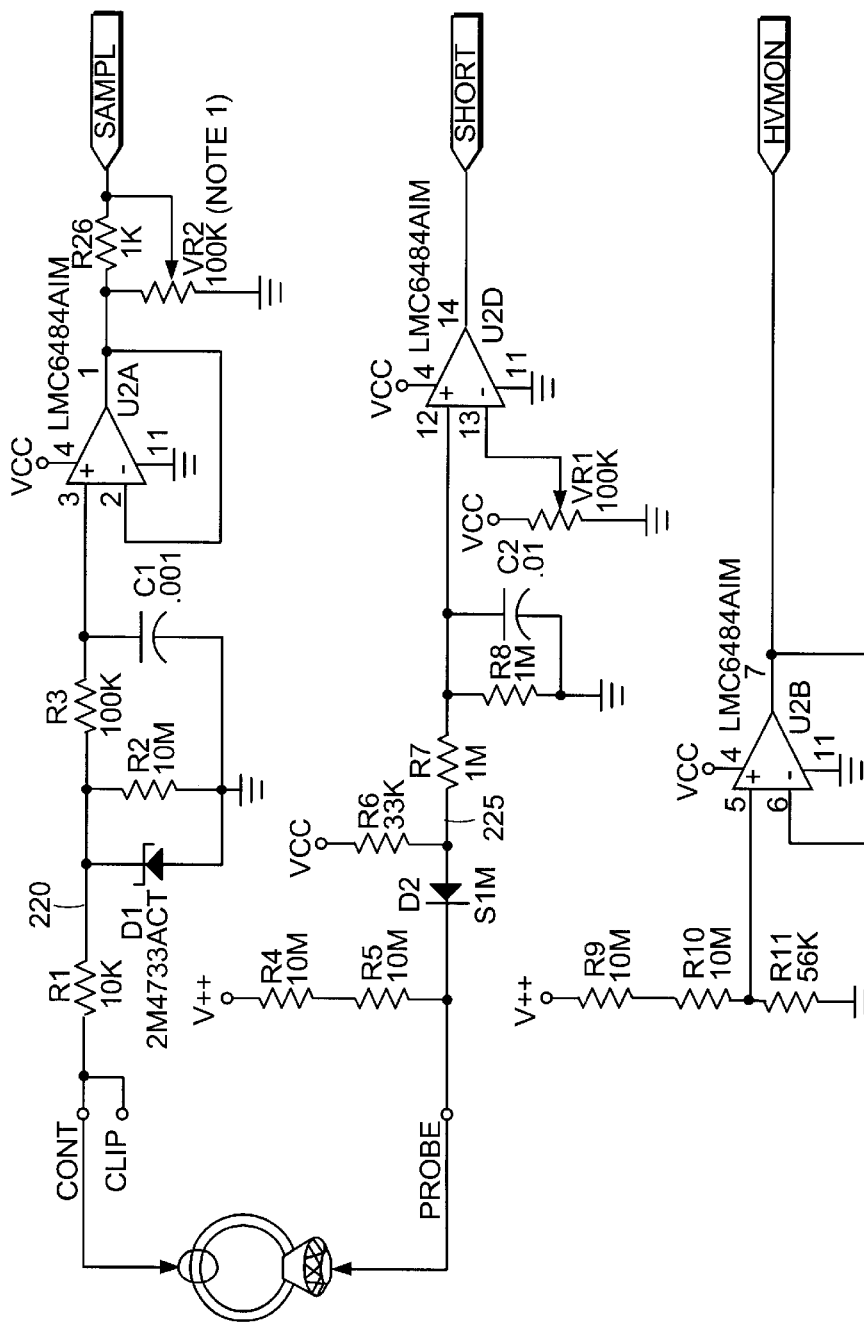
FIG. 2B is an electronic schematic of the inventive electrical conductivity circuitry and high voltage monitor.

FIG. 2B illustrates the electrical components of the high voltage monitor and critical portion of the gem tester circuitry. The high voltage monitor circuitry includes a voltage divider circuit, specifically the combination of resistors R9, R10 and R11, to reduce the voltage at U2B pin 4 to a voltage proportional to high voltage, i.e., 900–1000 VDC. This proportional reduction of voltage through a divider circuit serves to protect the input of op-amp U2B by converting the high V++ voltage to a proportional voltage between approximately 0 and 2.5 volts, an acceptable conversion range for the A/D converter. Otherwise, the high voltage input would damage the op-amps input U2B pin 5. Alternatively, if this high voltage was fed directly into the micro-controller U1 instead, the high voltage would damage the A/D converter within the micro-controller U1.

Operational amplifier U2B is configured as a unity gain buffer. This means that the output, U2B pin 7, effectively follows the input voltage at pin 5. This signal, connected to micro-controller U1 at pin 18, serves as a means of testing the health of the high voltage source, V++. For example, a voltage greater than 2.0 volts at U2B pin 7 indicates to the microcontroller U1 that the voltage at V++ is around 800 volts, presumably an acceptable voltage to perform gem measurement tests. A voltage less than 1.5 VDC indicates a high voltage V++ round 600 volts, suggesting that the unit is malfunctioning and, therefore, any test measurements would not be reliable.

The critical portion of the gem tester circuit in FIG. 2B is a two part circuit. A first part of the circuit produces a high impedance output voltage on signal PROBE, where a processor readable signal called SHORT indicates whether the probe and clip electrode contacts are erroneously shorted to each other. A second part of the circuit provides a highimpedance return path for the high impedance source voltage at the probe, which produces a current that flows through the gem under test. Effectively, the voltage produced at the clip, specifically the voltage produced at R2, is measured by the microcontroller U1 to determine the conductivity of the gem and whether it is moissanite or a synthetic diamond stone. The entire circuit is discussed in more detail below.

Fundamentally, the gem testing circuit in FIG. 2B uses a resistor voltage divider theory to determine the conductivity of the gem under test disposed between the clip and probe contact. For the purposes of the following discussion, unless otherwise stated, assume that a gem mounted within a conductive setting, such as gold or silver, is connected between the probe and clip of the gem testing device. Specifically, the clip is connected to the metallic portion of the setting and the probe is in contact with the surface of the gem under test.

High voltage source, V++, is connected to the surface of the gem under test through high impedance R4 and R5. When the gem under test is conductive, current flows through R4 and R5, the gem under test, the metallic setting of the gem, the clip, R1 and R2, to a ground reference voltage. Zener diode D1 limits the voltage at node 220 or R2 to less than +5V. Otherwise, the voltage on the node would exceed an acceptable limit if the probe and clip were accidentally shorted to each other. For example, R4, R5 and R6 would create a voltage such that ⅓ of the high voltage source or 330 volts would be produced at node 220.

The signal SHORT on the output of op-amp U2D provides the micro-controller U1 with a voltage indicative of whether the clip and probe are erroneously shorted. The circuit keys off the reduction in voltage on node 225 that occurs when the clip/probe are shorted. Current flows through D2, thereby creating a voltage drop across R36 which, in turn, is fed into threshold detector U2D pin 12 through voltage divider R7 and R8. When no short is present, no current flows through R36 other than through high impedance path R7 and R8. Hence, the voltage at 225 is higher than when a short is present across the clip and probe.

The threshold for a SHORT is set by controlling potentiometer VR1. It creates a reference voltage at the negative input of op-amp U2D pin 13. In the preferred embodiment, the reference threshold voltage is set via VR1 such that SHORT indicates a shorted probe to clip when the impedance between the probe/clip is less than around 3 to 10 kilo-ohms. However, it is optionally adjusted to different settings depending on the gem type tested.

The SHORT signal output produces a high output voltage of +5V when there is no shorted condition, and 0 volt output when there is a short or low impedance condition across the clip and probe. If a voltage on SHORT indicates a low impedance condition, a buzzer is sounded to alert the operator that the probe and clip are erroneously contacting each other or, alternatively, that the impedance of the gem under test is so low that it is likely not moissanite or a synthetic diamond stone. When a gem is disposed between the clip and probe, the SHORT signal will be de-asserted indicating that the voltage on SAMPL can be read to determine whether the gem under test is moissanite or a synthetic diamond stone.

A second part of the circuit shown in FIG. 2B provides the micro-controller U1 with a voltage signal indicative of whether a gem under test is moissanite or a synthetic diamond stone. When a stone such as natural diamond or cubic zirconia is tested, current flowing through the gem under test will produce a voltage on R2, which is filtered by low pass filter R3 and C1. This filter helps reduce high frequency AC noise on the measured signal. The voltage on R2 is effectively fed into a unity gain amplifier circuit at U2A pin 3, where the output of U2A pin 1 follows the voltage on U2A pin 3. This creates a low impedance SAMPL signal that is fed into an A/D converter within micro-controller U1. The combination of resistor R26 and variable resistor VR1 provide a means of calibrating the SAMPL voltage and associated electronic circuitry.

In an ideal operating environment, there is no AC noise that couples onto the high impedance voltage signal at R2. The circuit, therefore, is best understood by first analyzing its DC operation.

Consider the case when a natural diamond is the gem under test. Natural diamonds are virtually non-conductive. therefore, the measurement of SAMPL will be zero volts when the diamond is disposed between the clip and probe since no current from the high voltage source V++ passes through the stone to produce a voltage on R2.

On the other hand, consider the case where a SiC stone is the gem under test. The high voltage source provides the voltage to break down the SiC such that the gem becomes slightly conductive. Based on the steady state characteristics of the circuit, greater than 300 VDC is provided across the gem under test, meeting the breakdown voltage requirement of moissanite where current will flow through the gem. Synthetic diamonds also have a very high impedance between 1 and 20,000 megaohms. However, the synthetic diamond gem allows a sufficient current, although it is very small and on the order of micro-amps, to flow such that a voltage is produced at R2 when the gem is properly disposed between the clip and probe.

A threshold is set in the micro-controller U1 to determine if the gem under test is moissanite or a synthetic diamond. If the voltage at R2, or SAMPL, is greater than 0.5 VDC, the gem is determined to be moissanite or a synthetic diamond stone. Voltages above the 0.5 Volt threshold correspond to gem resistances of less than 20,000 mega-ohms.

If a body comes in contact with the clip and probe simultaneously, the gem tester will likely read a voltage similar to that for moissanite or synthetic diamond since the resistance of human skin is high like moissanite, but not nearly as high as natural diamond. It is also possible, depending on the setting of VR1, that the human skin measurements with the gem tester read as a short across the probe and clip electrodes.

The aforementioned discussion describes the operation of the gem tester circuit under ideal conditions, i.e., without AC noise. Typically, an operator in contact with the preferred embodiment hand-held probe imparts an AC noise signal which is superimposed on the DC sample voltage. This is due to the high impedance on both the probe and clip electrodes. As a result of these high impedance source and return paths, a body in contact with the gem, metal setting, clip, probe or gem tester housing will induce on AC noise on the DC voltage produced by the voltage divider circuit. Such an AC noise voltage riding on the DC sample voltage is usually less than 1 volt peak to peak. However, the intensity may be more or less depending on the environment. Typically, the frequency of the noise is less than 120 Hertz, but it may include higher frequencies such as RF. R3 and C1 act as an RF filter to block higher frequency noise picked up by the clip and probe assembly.

As a result of the AC coupled noise, it is necessary to sample the SAMPL voltage to determine whether a gem is moissanite or a synthetic diamond stone. In the preferred embodiment, the voltage SAMPL is sampled every 500 $\mu$S. If 256 sample readings in a row indicate a voltage greater than the 0.5V threshold, the gem under test is determined to be moissanite or a synthetic diamond stone. Conversely, if so much as one sample out of 256 consecutive sample voltages is below the 0.5V threshold, it is presumed that the gem under test is not moissanite or a synthetic diamond since the impedance is so high that a voltage below the threshold is produced at R2.

Figure 4:
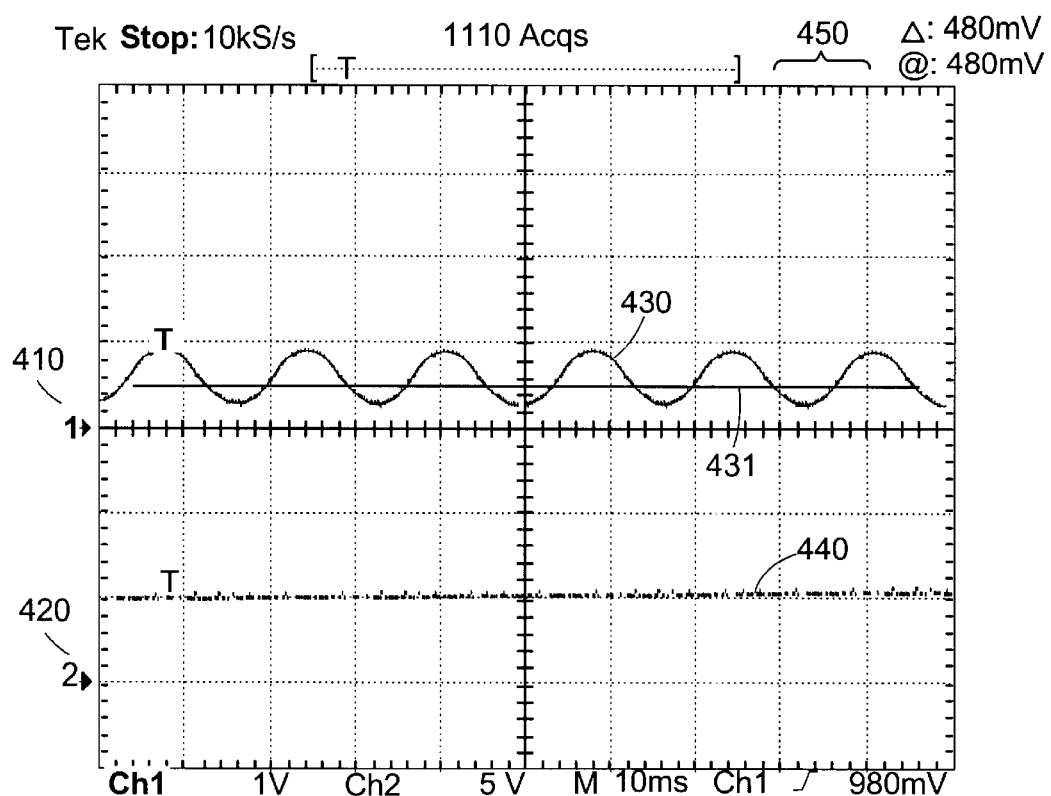
FIG. 4 is an illustration of a SAMPL voltage versus time graph where the gem tested is a diamond.

FIG. 4 shows a SAMPL voltage 430 on channel 1 versus time graph of a natural diamond being tested, where AC noise is coupled to the DC SAMPL signal. Channel 2 displays the SHORT signal 440, indicating that there is not a short circuit across the electrodes. Ground references are located at marking 410 and 420 as shown. In the preferred embodiment, sampling of the SAMPL 430 voltage signal will be performed every 0.5 milliseconds resulting in 20 samples per time division 450.

A DC component of 0.5V is present on the SAMPL signal 430 due to leakage current through oil or contaminants on the gem or tester body itself. The sample voltage 430 corresponding to the diamond as shown would not test positively as moissanite or a synthetic diamond stone because several sample points are below the 0.5 VDC threshold 431. To test positively as moissanite, a predetermined number of successive samples taken every 0.5 milliseconds must be above the 0.5 VDC threshold 431. In this case, many samples as shown are below the 0.5 VDC threshold 431 and, thus, it is determined that gem under test is not moissanite or a synthetic diamond.

It should be noted that the gem and setting should be thoroughly cleaned before testing because contaminants on the surface of the gem such as oil or metallic dust can be conductive, creating current leakage paths that cause erroneous gem tester readings. For example, current can flow through the contaminant instead of the gem under test, making it appear as though the conductivity of the gem is higher than it actually is.

Figure 5:
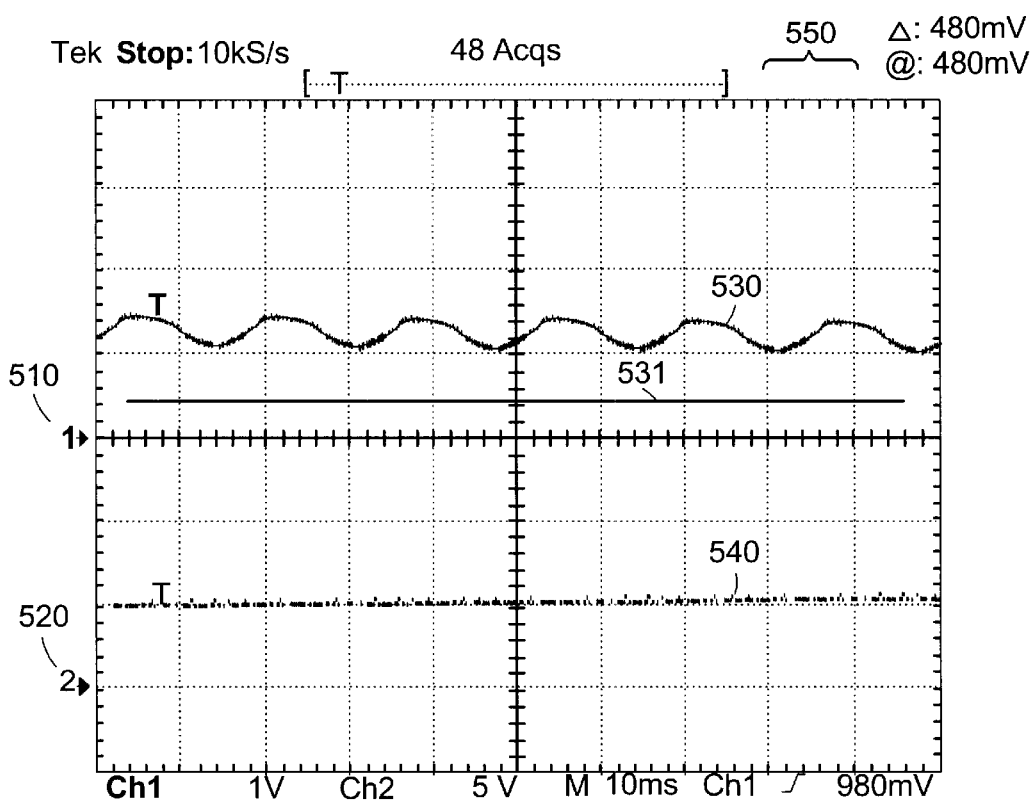
FIG. 5 is an illustration of a SAMPL voltage versus time graph where the gem tested is synthetic.

FIG. 5 shows a SAMPL voltage 530 on channel 1 versus time graph of a moissanite gem being tested, where a little AC noise is coupled to the DC SAMPL signal. Channel 2 displays the SHORT signal 540, in this case, indicating that there is not a short circuit across the electrodes. Ground references are located at marking 510 and 520 as shown. In the preferred embodiment, sampling of the SAMPL 530 voltage signal will be performed every 0.5 milliseconds resulting in 20 samples per time division 550.

Based on the SAMPL voltage 530 in this case, the micro-controller U1 sampling the sample voltage 530 would determine that the gem under test is moissanite or a synthetic diamond stone based on the fact that a predetermined number of consecutive samples of the voltage are consistently above the 0.5 VDC threshold 531, even though the AC waveform is also present.

Although unlikely, it is possible that the noise on the sampled signal is so great as to result in erroneous gem determination. Hence, it should be noted that the present invention produces a very high likelihood whether a gem is moissanite or a synthetic diamond because of the variability of some classes of stones and the high sensitivity of the tester itself, which can be misused.

For example, consider a synthetic diamond stone or moissanite that without noise produces a DC voltage of 1.0 volt. If AC noise coupling on to the signal is 2.0 volts peak to peak, the resulting AC and DC wave will be an approximate sinusoid fluctuating between zero and 2.0 volts. As a result, the sampling device will detect a voltage below the 0.5 volt threshold and, therefore, fail to determine that the gem under test is moissanite or a synthetic diamond, even though it is possibly either one of these composites. The gem tester device optionally uses an processing method in software to determine cancel the AC noise, so as not to be fooled by the additional AC noise effects.

It should be noted that moissanite stones sometimes have "dead" zones where the gem tester apparatus measurements will register as if the gem were not moissanite or a synthetic diamond stone. To enhance conductivity between the probe and surface of the gem under test, an electrically conductive substance, such as a mark from a water based marker, is placed on the gem under test where the probe is to be contacted. This technique helps avoid mistaking moissanite or synthetic diamonds for non-conductive gems such as natural diamond because the conductive mark bridges the moissanite "dead" zones with a conductive material.

Figure 2C:
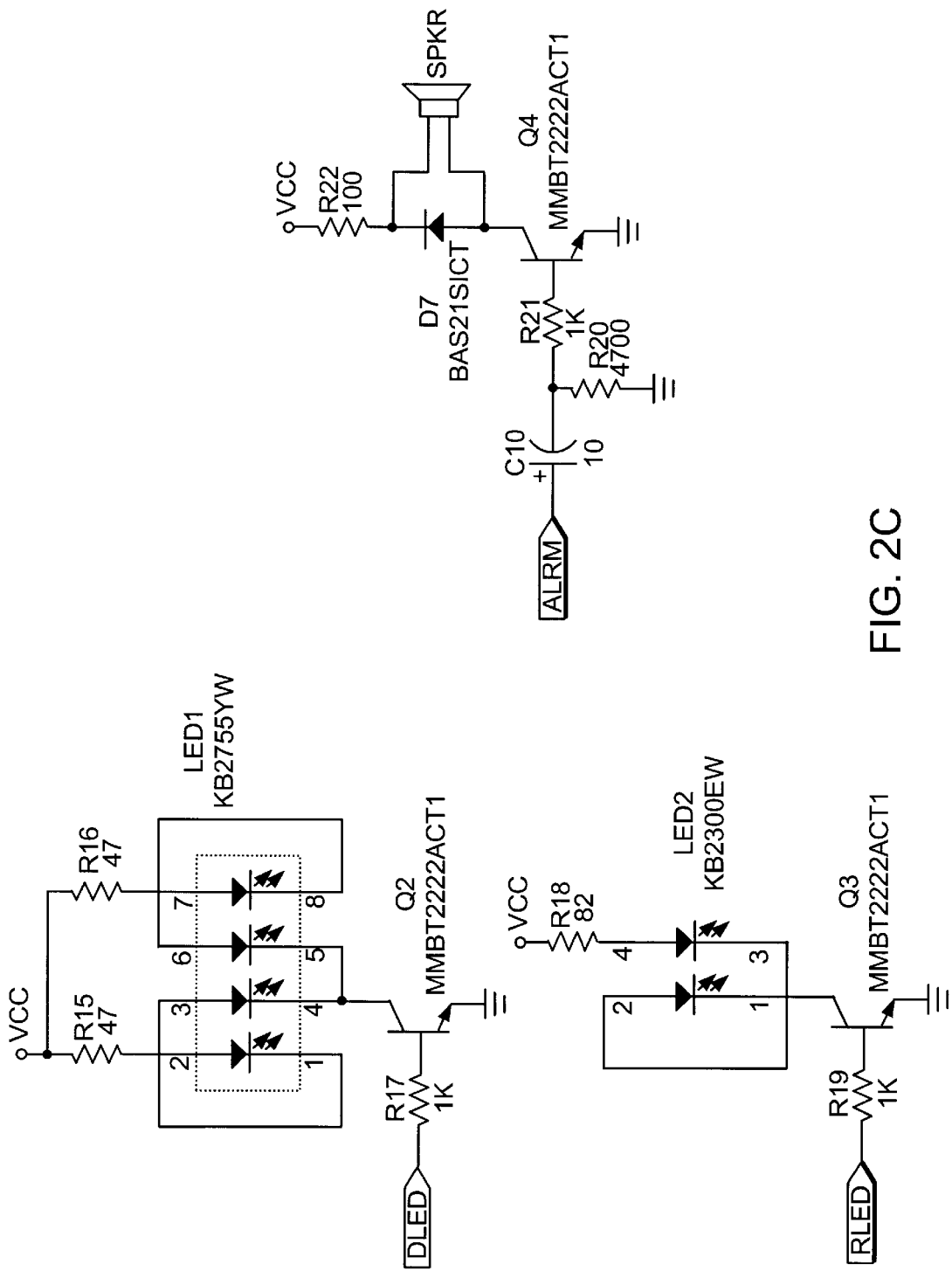
FIG. 2C is an electronic schematic of the inventive audio and visual display drivers of the present invention.

FIG. 2C illustrates the audio/visual electronic drive interface. For example, output signals of the micro-controller U1 by themselves are not robust enough to light an LED display or cause a speaker to emit sound. Therefore, micro-controller U1 signals DLED, RLED and ALRM are fed into the input of an NPN transistor such as Q2, Q3, and Q4, to amplify the original signal, creating a number of high current sinking elements, i.e., the collector of Q2, Q3, and Q4, for controlling the audio and visual displays. To achieve a gradient voltage effect at the output device, the binary micro-controller output signals DLED, RLED, and ALRM, are optionally pulse width modulated between 0 and 100% to vary the intensity of light from the LED or sound out of the speaker. The speaker effectively imitates the sound of a buzzer, alarm, or optionally, the sound of a human voice.

Figure 2D:
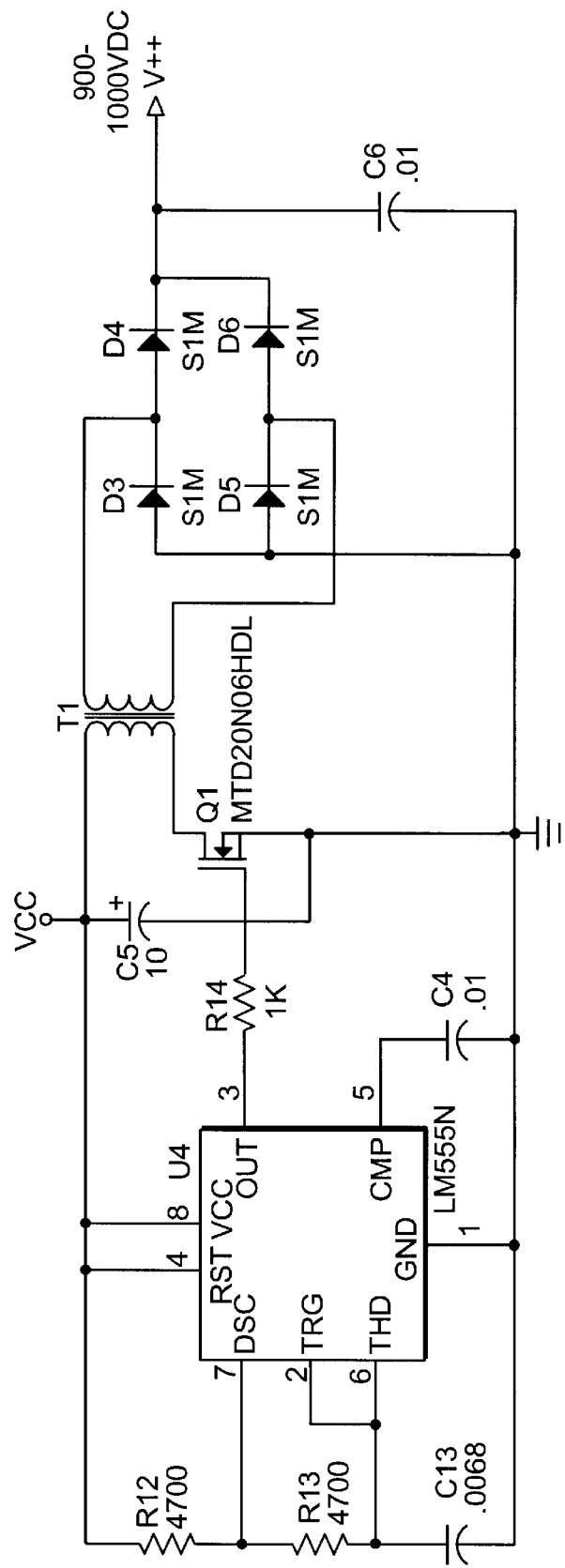
FIG. 2D is an electronic schematic of the high voltage DC-DC converter in the present invention.

FIG. 2D illustrates the preferred embodiment of the high voltage DC-DC converter. Put simply, the combination of components converts a +5 VDC or Vcc input to a high voltage output source V++ near 1000 VDC, as in the preferred embodiment. Based on the selected components, the output voltage V++ is around 900–1000 VDC. The components, however, are optionally adjusted to produce an acceptable higher or lower voltage level for testing gem stones.

Clock timer U4 produces a predictable oscillating voltage output at pin 3 that effectively controls the gate input to FET switch Q1. This voltage is a square wave with an "ON" duty cycle usually between 50 and 90%. A high voltage turns the switch to the on state, causing a current to flow through the primary coil of transformer T1. Conversely, a low voltage at gate input to FET switch Q1 causes the switch to turn off, restricting the current flowing through the primary coil of transformer T1. The change in current resulting from switching Q1 "ON" and "OFF," as well known, induces a current and voltage to be produced at a secondary coil on transformer T1. Based on a greater number of coil windings in the secondary coil, a proportionally higher voltage is produced across the secondary winding of T1. Diodes D3 through D6 serve to rectify the signal such that a high DC voltage is produced at the output V++. Miscellaneous resistors and capacitors serve to optimally set the switching frequency of transistor Q1. C5 is an electrolytic capacitor that buffers the voltage VCC during times of high current draw such as when Q1 is turned "ON."

Figure 2E:
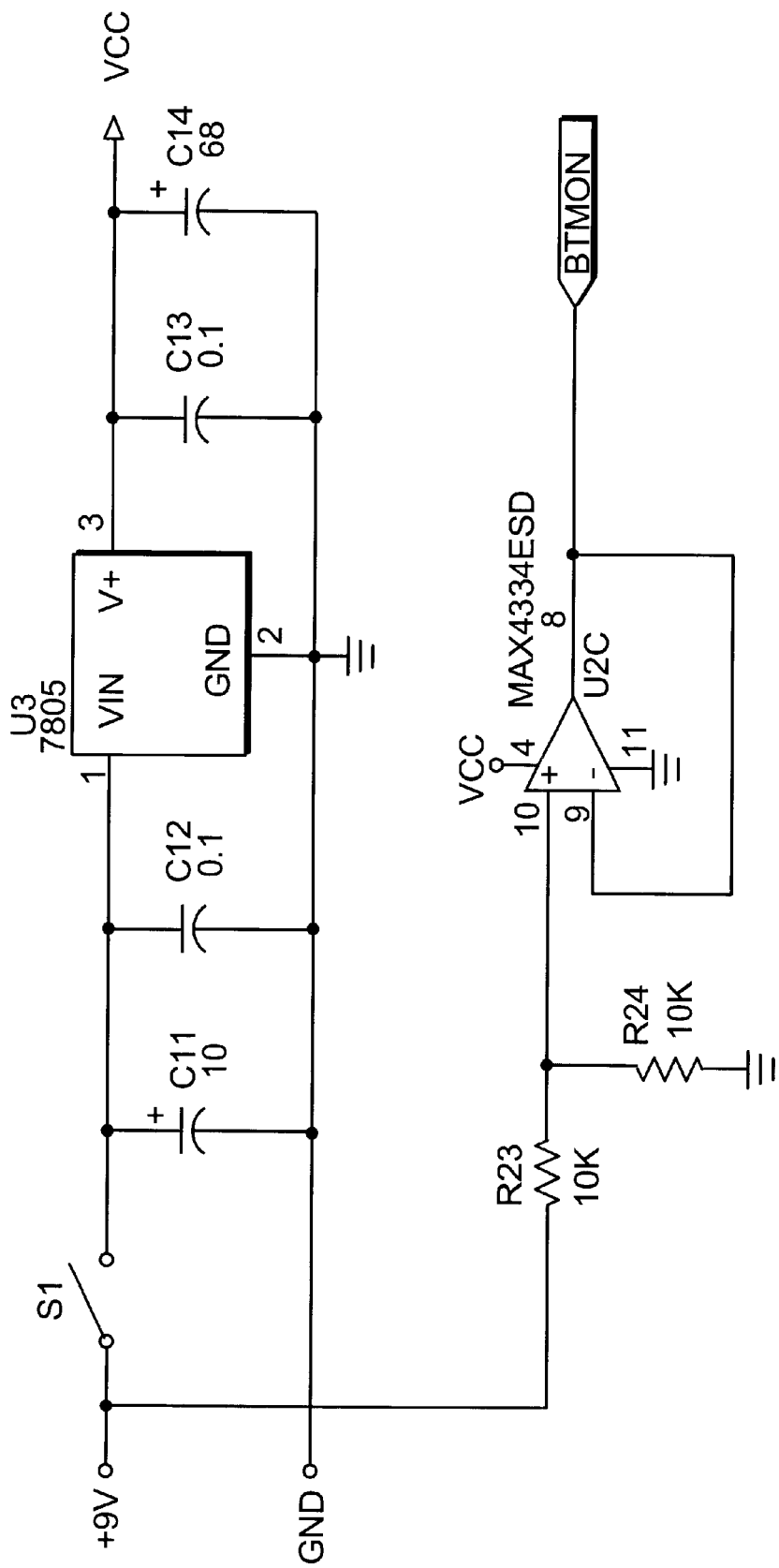
FIG. 2E is an electronic schematic of the On-OFF switch, regulator and battery voltage monitor of the present invention.

FIG. 2E illustrates the switch input for powering the gem tester circuitry and the voltage regulator that converts the +9V source power to an acceptable voltage level output Vcc, which is typically +5 VDC. Switch S1 is a single pole switch providing connectivity of the +9V source power to the regulator voltage input U3 pin 1. When the switch S1 is thrown to the "ON" position, the +9V source power voltage is effectively converted to +5 VDC or Vcc at the output U3 pin 3. This voltage is optionally adjusted to accommodate lower voltage circuit designs such as +3 VDC microcontroller systems.

FIG. 2E also includes a conditioner circuit for converting the +9V source voltage 120 to a proportional voltage that is monitored by micro-controller U1. The +9V source power is divided in half by R23 and R24, where the resulting signal is fed into a unity gain amplifier circuit. Thus, the proportional voltage on the output of unity gain amplifier U2C provides the microcontroller U1 a voltage reflective of the +9V source power, thereby enabling the microcontroller to determine the health of the +9V source input 120. If the voltage at the +9V source 120 is below a threshold, such as 7.5V, the gem tester unit will not attempt to test a gem since the input voltage is too low.

Figure 3A:
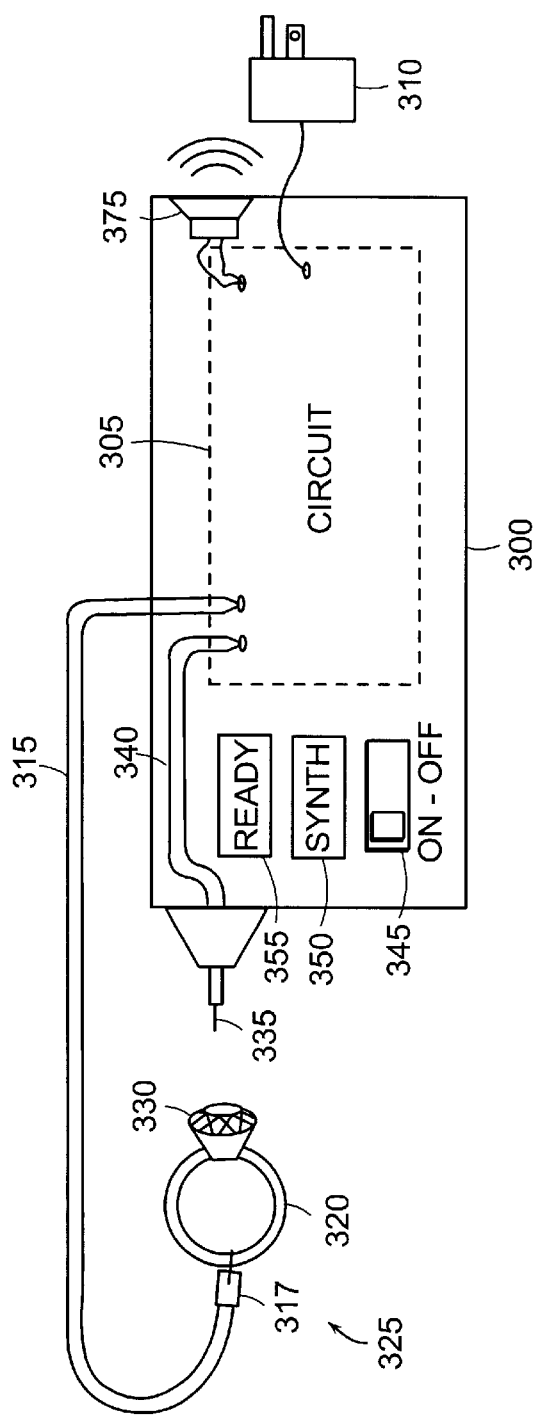
FIG. 3A is a diagram of the handheld probe and associated and associated hardware of the present invention.
Figure 3B:
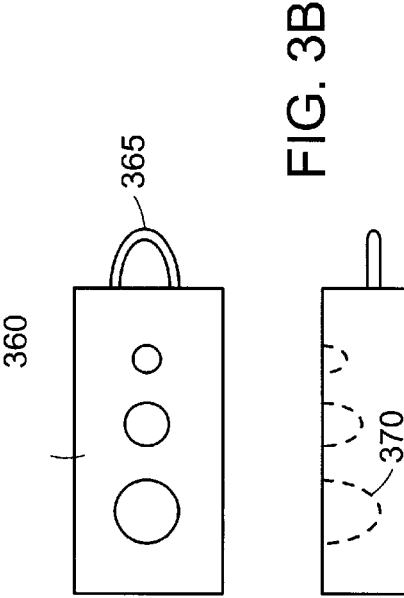
FIG. 3B is a conductive block used to retain and test loose gems with the inventive gem tester device.

FIG. 3A illustrates the gem tester housing 300 protecting the electronic circuitry 305 and associated hardware. A wall adapter 310 provides the +9V source 120 power to the electronic circuit 305 depending on the position of the ON-OFF switch 345. As mentioned, the power source is optionally a battery.

The gem tester requires two points of contact on the gem to determine whether the gem under test 330 is SiC or a synthetic stone. A first point of electrical contact is made with alligator clip 317, which grips the metallic band 320 of diamond ring 325. The metallic band 320 is in electrical contact with the stone, hence, alligator clip 317 and metallic band 320 form the first low impedance contact with the gem under test 330. Highly conductive clip wire 315 translates this voltage, via a wire, back to the electronic circuitry 305 in the gem tester housing 300.

A second contact point with the gem under test 330 is made by moving the handheld probing device in contact with the purported diamond ring 325 so that the gem under test 330 is in contact with push pin 335 mounted on the base of the housing 300. In the preferred embodiment, the conductive push pin 335 is spring-loaded to aid in making a connection with the gem 330 being tested and rigidly mounted on the distal end of the housing as shown. The push pin wire 340 is connected to push pin 335 at one end, while the push pin wire 340 is connected to the electronic circuitry 305 at the other end. It should be noted that the push-pin 335 is optionally designed to reside in a hand-held probing device connected by a cable to the main housing 300.

The gem tester 300 includes both audio and visual displays. LEDs or lights provide an illumination source for READY display 355 and SYNTH (short for "synthetic") display 350, the latter display indicating that the gem is moissanite or a synthetic diamond when lit. Electronic circuit 305 drives the light source, where READY indicates to the operator that the unit is ready to test a gem and the unit is turned ON. When results of a gem test indicate that it is moissanite or a synthetic diamond, the SYNTH display 350 is illuminated by electronic circuitry 305.

Speaker 375 is activated to produce a buzzing sound if the metallic band or alligator clip 317 is accidentally contacted to push pin 335. In this case, a gem reading is invalid because the gem tester determines whether the gem under test 330 is moissanite or a synthetic diamond gem stone based upon two contact points across the gem, not two contact points across the electrically conductive band 320. In the aforementioned case of a shorted clip to probe, a buzzer sound from the speaker 375 notifies the user that the gem tester 100 is not being operated properly and, specifically, that the probe 335 and clip 317 are being misused. While a gem is properly connected as described above and the SYNTH display 350 is not lighted and buzzer is not sounded, this indicates to the operator that the purported diamond ring 325 is likely a cubic zirconia or natural diamond. Further testing, for example, with a thermal gem tester is used to distinguish these gems apart.

The aforementioned discussion describes how an operator tests a purported diamond ring 325, including a metallic band 320, wherein the gem under test 330 is encased in a proper jewelry setting. The present invention also accommodates testing of loose gemstones by incorporating additional hardware to hold an "un-set" gem under test. Conductive block 360 made of metal, such as aluminum, includes multiple holes 370 to hold variably sized loose gems.

To test a gem, the operator places the gem in the appropriate sized holes 370 to snugly form a first electrical contact with the gem. Alligator clip 377 is connected to fastener contact point 365 and probe 335 is moved to contact the gem under test. Effectively, the conductive block simulates a jewelry setting for the loose stones, where the conductive block 360 provides good conductive contact with the gem under test at one or multiple points and the push pin 335 contacting the surface or second point on the gem provides the other.

Figure 6A:
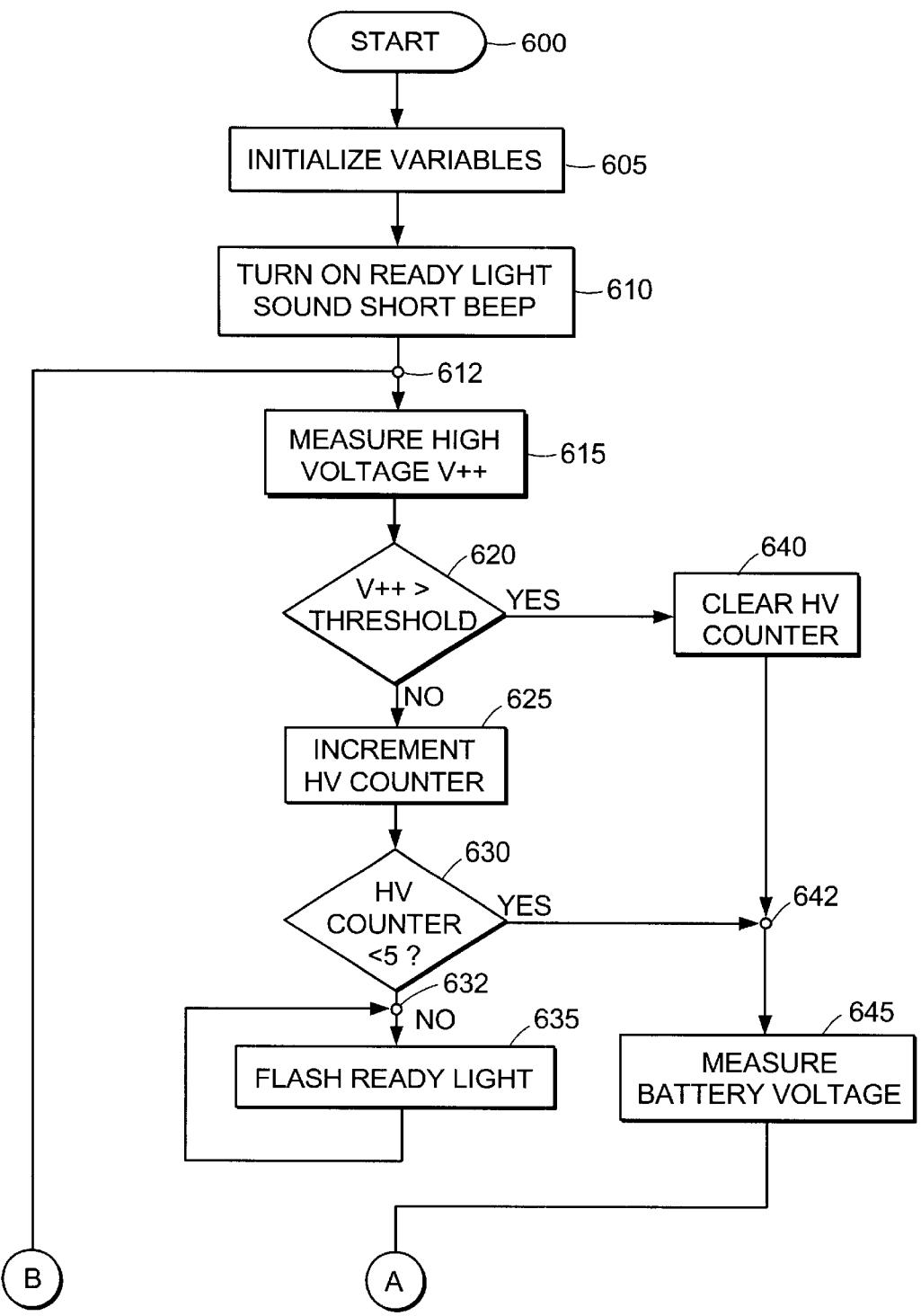
FIGS. 6A, 6B, and 6C illustrate the inventive methodology used to determine whether a gem is synthetic.
Figure 6B:
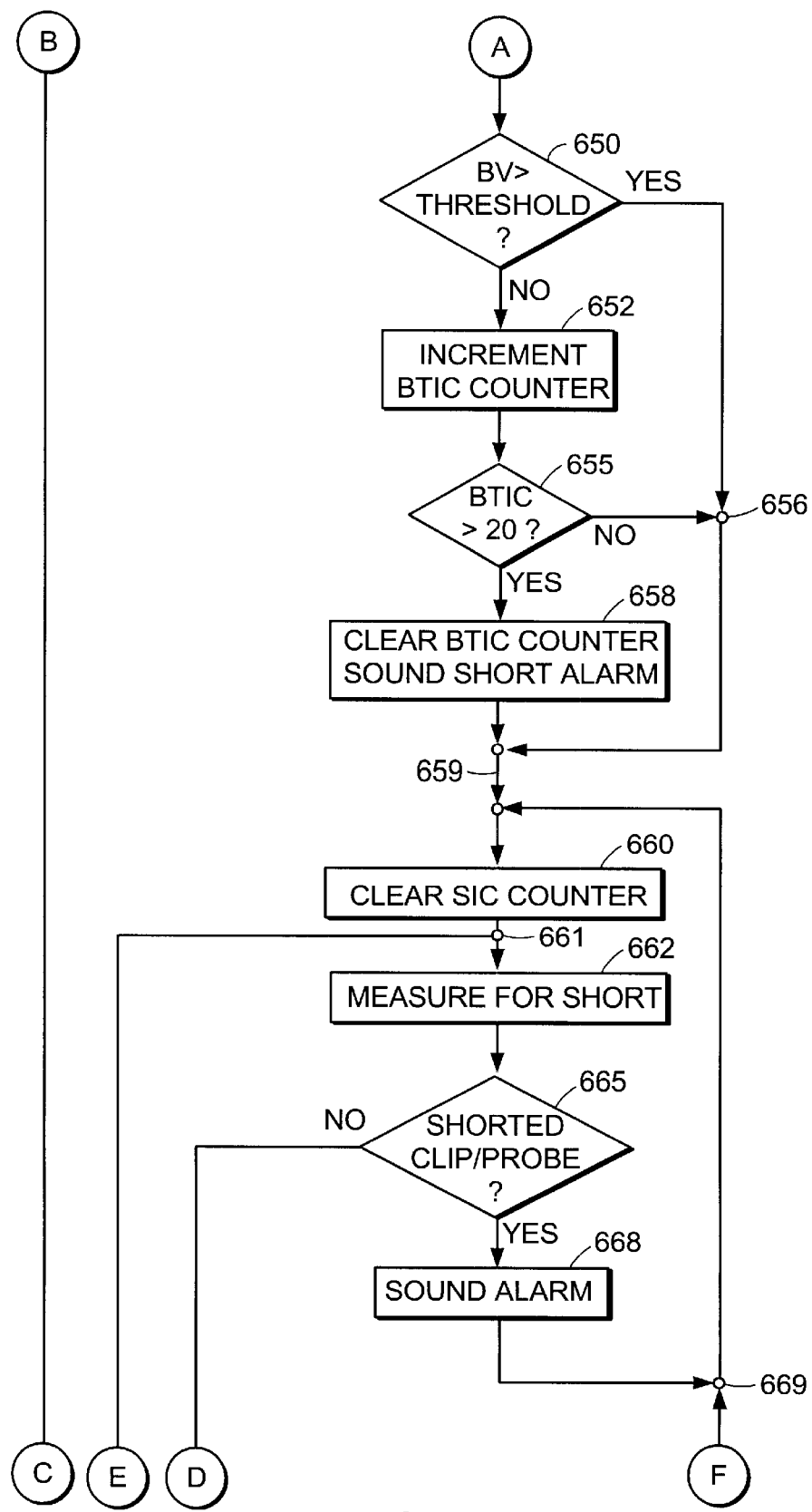
Figure 6C:
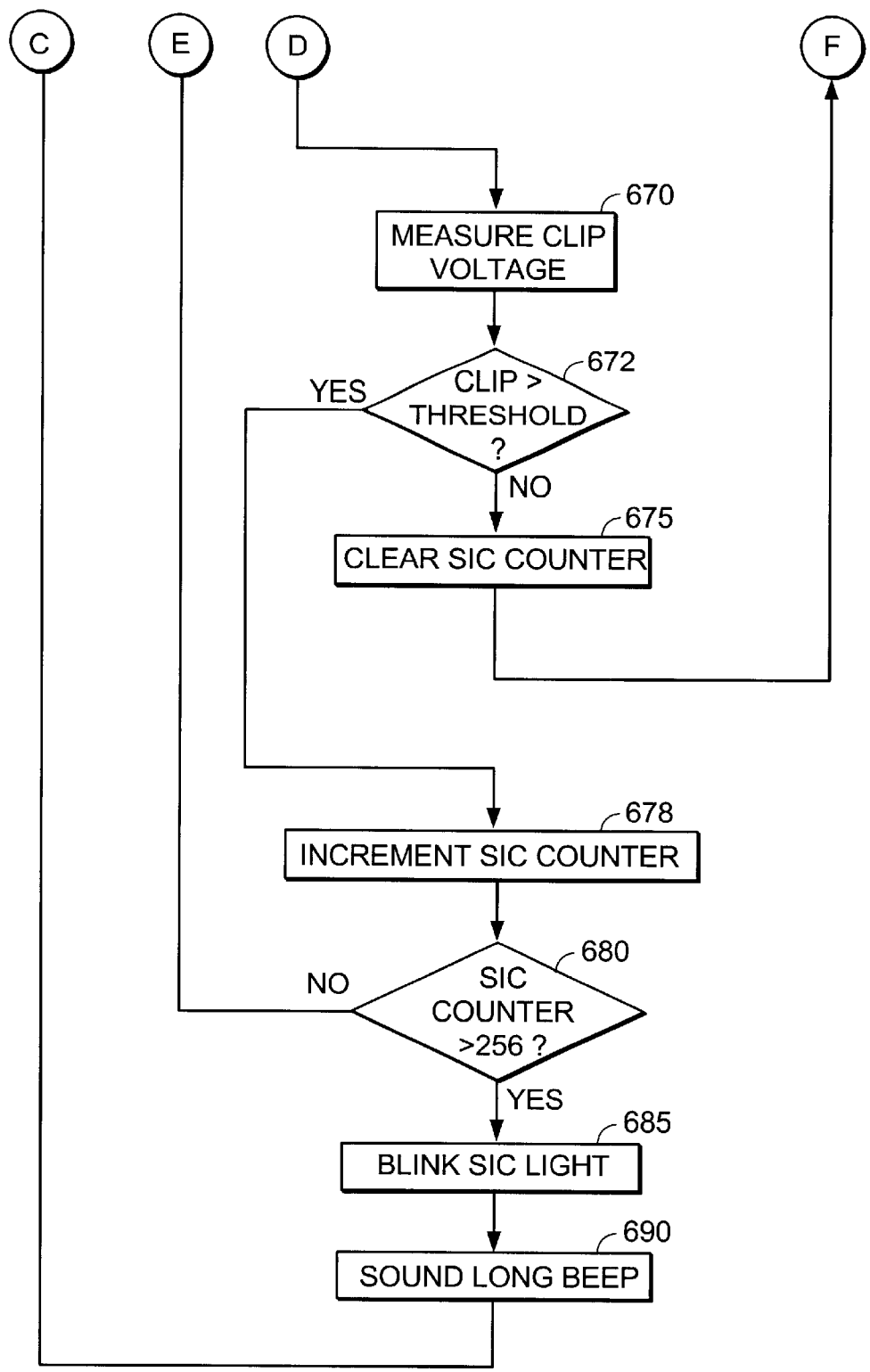

FIGS. 6A, 6B and 6C illustrate the method used to determine whether a gem under test is moissanite or a synthetic diamond. The flow chart provides the basic architecture of the software operations executed in the micro-controller.

Immediately after powering the gem tester, the program is executed from START in step 600. Variables used in processing digital signals are initialized in step 605 and the READY light is turned to the "ON" state followed by a short beep in step 610. This queues the operator that power has been turned "ON" and the software in the micro-controller is being executed to determine whether a gem under test is moissanite or a synthetic diamond.

The software comprises four major processing functions. The first involves testing the high voltage power source V++, which is measured in step 615. If the voltage of the high voltage source is not above a specified threshold in step 620, the HV counter is incremented in step 625. If the HV counter then exceeds a predetermined number, such as 4, in step 630, the READY light is continuously flashed in step 635, indicating that the high voltage source is malfunctioning. The program thereafter loops back on itself at point 632 as shown.

If the high voltage measured on step 615 is greater than a tolerable threshold in step 620, the high voltage or HV counter is cleared in step 640. The program path then merges at point 642, where the program ends up if the high voltage counter is less than 5 in step 630. Based on this routine, the gem tester continues testing even if power on the high voltage experiences an occasional glitch. However, if the voltage at the high voltage source is always low, there is a problem with the electronic circuitry in the gem tester unit.

The next step 645 involves measuring the battery voltage. If the measured battery voltage is less than a tolerable threshold as in step 650, the BTIC counter is incremented by one in step 652. The BTIC counter indicates the number of failed battery monitor tests. It is thereafter determined in step 655 whether the BTIC counter is greater than 20. If so, the BTIC counter is cleared and a short alarm is sounded in step 658. This audio queue notifies the gem tester operator that the battery power source is getting low. If the battery voltage measurement is greater than the threshold in step 650 or BTIC counter is less than 20 in step 655, the program execution merges to point 656.

The SiC counter is then cleared in step 660 and the SHORT signal input is measured in step 662. If there is a shorted condition across clip and probe in step 665, an alarm is sounded in step 668. This notifies the operator that the probe and clip are erroneously touching or that a low impedance material is disposed between the clip and probe. As shown, the software execution does not leave the SHORT test loop until the shorted condition is corrected.

If the clip/probe is not shorted in step 665, a SAMPL measurement is made in step 670. It is then determined whether the SAMPL voltage is greater than a predetermined threshold in step 672 indicating that the gem under test is moissanite or a synthetic diamond. In the preferred embodiment, this voltage threshold is set to 0.5V. If the SAMPL voltage is less than the threshold voltage, the SiC counter is cleared in step 675 and program execution continues at point 669 to step 660. If the SAMPL voltage is greater than the threshold voltage, the SiC counter is incremented in step 678.

It is thereafter determined in step 680 whether the SiC counter is greater than 256. If so, the SiC flashes and long beep is sounded in steps 685 and step 670, respectively. This provides an audio an visual queue to the operator that the gem under test is moissanite or a synthetic diamond. Program execution, thereafter, continues near the beginning at point 612. If the SiC counter is less than 256 in step 680, program execution continues at step 661, where SAMPL measurements are repeated to determine whether the gem under test is moissanite or a synthetic diamond.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. An apparatus for distinguishing gems based on their electrical conductivity, the apparatus comprising:
    a first contact electrically coupled to a first point on a surface of a gem under test;
    a second contact electrically coupled to a second point on the surface of the gem under test, the first and second contacts providing a circuit path through the gem under test; and
    an electronic circuit connected to the first and second contacts for measuring a voltage across the gem under test proportional to an electrical conductivity of the gem under test to provide an indication of its type, the circuit including a high impedance, high voltage source providing a voltage greater than 300 volts across the gem under test based on a voltage at the first contact and corresponding return current path at a second contact.

2. An apparatus as in claim 1 wherein the high impedance, high voltage source limits current through the first and second contacts to less than 150 microamps when short circuited.

3. An apparatus as in claim 2 wherein the current through the first and second contacts is less than 75 microamps.

4. An apparatus as in claim 2 wherein the electronic circuit includes a circuit for detecting a low impedance between the first and second contacts.

5. An apparatus as in claim 4 wherein a sampling circuit repeatedly measures a voltage across the gem under test, including stray AC noise, to determine a gem type based on conductivity.

6. An apparatus as in claim 1 wherein the electronic circuit includes a circuit for detecting a low impedance between the first and second contacts.

7. An apparatus as in claim 6 wherein a sampling circuit repeatedly measures a voltage across the gem under test, including stray AC noise, to determine a gem type based on conductivity.

8. An apparatus as in claim 1 wherein a sampling circuit repeatedly measures a voltage across the gem under test, including stray AC noise, to determine a gem type based on conductivity.

9. An apparatus as in claim 1 wherein a loose gem under test is placed in a hole in a conductive block and one contact touches the conductive block and another contact touches the surface of the gem under test to complete a circuit path including the gem under test and conductive block between the first and second contact.

10. An apparatus as in claim 1 wherein a conductive substance, marked on the surface of the gem where contact is made with the first or second contact, provides a highly conductive path between the surface of the gem under test and corresponding contact.

11. An apparatus as in claim 1 wherein the electronic circuit includes a resistance voltage divider including the gem under test as part of the resistance voltage divider.

12. An apparatus as in claim 1 wherein the gem under test is mounted in a conductive metal structure to retain the gem under test, the first contact touching a first point on the surface of the gem under test and the second contact touching the conductive metal structure retaining the gem under test where current flowing through the conductive metal and gem is measured by the electronic circuit to determine the conductivity of the gem.

13. An apparatus as in claim 1 wherein the return current path at the second contact includes a high impedance to a reference voltage.

14. An apparatus as in claim 1 wherein the voltage at the second contact is measured to determine the conductivity of a gem being tested.

15. An apparatus as in claim 1 wherein the electronic circuit includes a device to repeatedly sample a voltage which is compared to a predetermined threshold indicating conductivity and gem type.

16. An apparatus as in claim 12 wherein the gem under test and conductive metal structure is a gem in a jewelry setting.

17. An apparatus as in claim 12 wherein the electronic circuit measures the voltages at the second contact to determine the conductivity of the gem under test.

18. An apparatus as in claim 1 wherein the electronic circuit measures the current through the gem to determine the type of gem.

19. An apparatus as in claim 1 wherein the voltage of the high voltage source at the first contact is between about 900 and 1000 volts.

20. An apparatus as in claim 12 wherein the electronic circuit detects when the first and second contact both come in contact with the conductive metal structure retaining the gem under test and an audible tone is provided to signal this condition to an operator.

21. An apparatus as in claim 12 wherein the electronic circuit detects when the first and second contact both come in contact with the conductive metal retaining the gem under test and a visual queue is provided to signal this condition to an operator.

22. An apparatus as in claim 1 further comprising: a visual display for displaying the type of gem detected.

23. An apparatus as in claim 1 capable of determining whether the gem under test is synthetic.

24. An apparatus for distinguishing gems based on their electrical conductivity, the apparatus comprising:
a first contact coupled to a first point on a surface of a gem under test;
a second contact coupled to a second point on the surface of the gem under tests the first and second contact providing a circuit path through the gem under test; and
an electronic circuit connected to the first and second contacts for applying a voltage across the gem under test, the electronic circuitry successively sampling the voltage across the gem under test including AC coupled noise and indicating a gem type when a predetermined number of samples are above a threshold voltage.

25. A method for distinguishing gems based on their electrical conductivity, the method comprising the steps of:
coupling to a first point on a surface of a gem under test with a first contact;
coupling to a second point on the surface of the gem under test with a second contact; and
providing an electronic circuit connected to the first and second contacts for measuring the conductivity of the gem under test between the first and second contacts including a device to measure voltages indicative of the conductivity of the gem under test; and
providing a software program that processes the measured voltages to determine whether the first and second contacts are shorted and, if not, the software program processing the measured voltage to determine whether a sample voltage is above a predetermined threshold indicating that the gem under test is synthetic.

26. A method for distinguishing gems based on their electrical conductivity, the method comprising the steps of:
coupling to a first point on a surface of a gem under test with a first contact;
coupling to a second point on the surface of the gem under test with a second contact, the first and second contact providing a circuit path through the gem under test;
providing electronic circuitry connected to the first and second contacts; and
measuring an electrical conductivity of the gem under test to provide an indication of its type based on a voltage at the first contact and corresponding return current path at the second contact, the electronic circuitry including a high impedance, high voltage source providing a voltage greater than 300 volts across the gem under test.

27. A method as in claim 26 wherein the high impedance high voltage source limits current through the first and second electrodes to less than 150 microamps when short circuited.

28. A method as in claim 27 wherein the current through the first and second contacts is less than 75 microamps.

29. A method as in claim 27 wherein the electronic circuitry includes a circuit for detecting a low impedance between the first and second contacts.

30. A method as in claim 29 wherein the electronic circuitry includes a sampling circuit that repeatedly measures a voltage, including stray AC noise, to determine a gem type based on conductivity.

31. A method as in claim 26 wherein the electronic circuitry includes a circuit for detecting a low impedance between the first and second contacts.

32. A method as in claim 31 wherein the electronic circuitry includes a sampling circuit that repeatedly measures a voltage, including stray AC noise, to determine a gem type based on conductivity.

33. A method as in claim 26 wherein the electronic circuitry includes a sampling circuit that repeatedly measures a voltage, including stray AC noise, to determine a gem type based on conductivity.

34. A method as in claim 26 wherein a loose gem under test is placed in a hole in a conductive block and one contact touches the conductive block and another contact touches the surface of the gem under test to complete a circuit path including the gem under test and conductive block between the first and second contacts.

35. A method as in claim 26 wherein a conductive substance, marked on the surface of the gem where a connection is made with a contact, provides a highly conductive path between the surface of the gem under test and corresponding contact.

36. A method as in claim 26 wherein the electronic circuitry includes a resistance voltage divider including the gem under test as part of the resistance voltage divider.

37. A method as in claim 26 wherein the gem under test is mounted in a conductive metal structure to retain the gem under test, the first contact touching a first point on the surface of the gem under test and the second contact touching the conductive metal structure retaining the gem under test where current flowing through the conductive metal and gem is measured by the electronic circuitry to determine the conductivity of the gem.

38. A method as in claim 26 wherein the return current path at the second contact includes a high impedance to a reference voltage.

39. A method as in claim 26 wherein the voltage at the second contact is measured to determine the conductivity of a gem being tested.

40. A method as in claim 26 wherein the electronic circuitry includes a device to repeatedly sample a voltage which is compared to a predetermined threshold indicating conductivity and gem type.

41. A method as in claim 37 wherein the gem under test and conductive metal structure is a gem in a jewelry setting.

42. A method as in claim 37 wherein the electronic circuitry measures the voltages at the second contact to determine the conductivity of the gem under test.

43. A method as in claim 26 wherein the electronic circuitry measures the current through the gem to determine the type of gem.

44. A method as in claim 26 wherein the voltage of the high voltage source at the first contact is between about 900 and 1000 volts.

45. A method as in claim 37 wherein the electronic circuitry detects when the first and second contacts both come in contact with the conductive metal structure retaining the gem under test and an audible tone is provided to signal this condition to an operator.

46. A method as in claim 37 wherein the electronic circuitry detects when the first and second contacts both come in contact with the conductive metal structure retaining the gem under test and a visual queue is provided to signal this condition to an operator.

47. A method as in claim 26 further comprising the step of:

displaying the type of gem detected on a visual display.

48. A method as in claim 26 further comprising the step of:

determining whether the gem under test is synthetic.

49. A method for distinguishing gems based on their electrical conductivity, the method comprising the steps of:

coupling to a first point on a surface of a gem under test with a first contact;

coupling to a second point on the surface of the gem under test with a second contact; and providing electronic circuitry connected to the first and second contacts for applying a voltage across the gem under test, the electronic circuitry sampling the voltage across the gem under test including AC coupled noise and indicating a gem type when a number of samples are above a threshold voltage.

50. An apparatus for distinguishing gems based on their electrical conductivity comprising:

means for electrically coupling to a first point on a surface of a gem under test;

means for electrically coupling to a second point on the surface of the gem under test; and means for measuring an electrical conductivity of the gem under test to provide an indication of its type, the measuring means including a high impedance, high voltage source providing a voltage greater than 300 volts across the gem under test based on a voltage at the first point on the surface of the gem under test and corresponding return current path at the second point on the surface of the gem under test.

* * * * *